(12) United States Patent
Greenblatt

(10) Patent No.: US 7,534,801 B2
(45) Date of Patent: May 19, 2009

(54) PIPERIDINYLCHROMEN-6-YLSULFONAMIDE COMPOUNDS AS 5-HYDROXYTRYPTAMINE-6 LIGANDS

(75) Inventor: Lynne Padilla Greenblatt, Lambertville, NJ (US)

(73) Assignee: Wyeth, Madison, NJ (US)

( * ) Notice: Subject to any disclaimer, the term of this patent is extended or adjusted under 35 U.S.C. 154(b) by 459 days.

(21) Appl. No.: 10/962,087

(22) Filed: Oct. 8, 2004

(65) Prior Publication Data

US 2005/0107431 A1 May 19, 2005

Related U.S. Application Data

(60) Provisional application No. 60/510,347, filed on Oct. 10, 2003.

(51) Int. Cl.
*A61K 31/4433* (2006.01)
*C07D 401/00* (2006.01)
(52) U.S. Cl. ........................... 514/320; 546/196
(58) Field of Classification Search ........... 546/196; 514/320
See application file for complete search history.

(56) References Cited

U.S. PATENT DOCUMENTS

| 4,363,811 A | 12/1982 | Evans et al. |
| 5,236,935 A | 8/1993 | Yoo et al. |
| 5,493,029 A | 2/1996 | Yoo et al. |
| 5,637,624 A | 6/1997 | Schaus et al. |
| 5,690,906 A | 11/1997 | Kung |

FOREIGN PATENT DOCUMENTS

| WO | WO 97/23209 A1 | 7/1997 |
| WO | WO 98/00412 A1 | 1/1998 |
| WO | WO 98/04542 A1 | 2/1998 |

OTHER PUBLICATIONS

Slassi et. al. "Recent Progress in the 5-HT6 receptor antagonists for the treatment of CNS diseases" Expert Opinion on therapeutic Patents 2002, 12, 513-527.*

Dorwald F.A. Side Reactions in Organic Synthesis, 2005, Wiley: VCH, Weinheim p. IX of Preface.*

Sulfonyl Chlorides Available from Sigma-Aldrich (created by examiner).*

Jörg Holenz, Petrus J. Pauwels, José Luis Díaz, Ramon Mercer, Xavier Codony and Helmut Buschmann "Medicinal chemistry strategies to 5-HT6 receptor ligands as potential cognitive enhancers and antiobesity agents" Drug Discovery Today 2006, 11, 283-299.*

Sethna, Suresh "Cycliacylation" Chapter XXXV in Friedel-Crafts and Related Reactions III Part 2, Ed. George A. Olah Wiley: New York, 1964, 911-997, 1000-1002.*

Terry Kenakin and Ongun Onaran "The ligand paradox between affinity and efficacy: can you be there and not make a difference?" TRENDS in Pharmacological Sciences 2002, 23, 275-280.*

Ellen S. Mitchell, John F. Neumaier "5-HT6 receptors: a novel target for cognitive enhancement" Pharmacology & Therapeutics 2005, 108, 320-333.*

* cited by examiner

*Primary Examiner*—Rita J Desai
*Assistant Examiner*—David K O'Dell
(74) *Attorney, Agent, or Firm*—Gloria K. Szakiel; Scott Larsen; David Kurlandsky

(57) ABSTRACT

The present invention provides a compound of formula I and the use thereof for the therapeutic treatment of a CNS disorder relating to or affected by the 5-HT6 receptor.

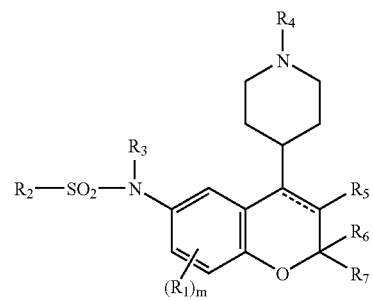

(I)

13 Claims, No Drawings

US 7,534,801 B2

PIPERIDINYLCHROMEN-6-YLSULFONAMIDE COMPOUNDS AS 5-HYDROXYTRYPTAMINE-6 LIGANDS

This application claims the benefit under 35 U.S.C. §119 (e) to co-pending U.S. provisional application No. 60/510,347, filed Oct. 10, 2004, which is hereby incorporated by reference in its entirety.

BACKGROUND OF THE INVENTION

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's.

The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; El Mestikawy, S. *Brain Research*, 1997, 746, 207-219). The ability of known 5-HT6 receptor ligands to enhance cholinergic transmission also supports the potential cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537-1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology*, 2000, 130(1), 23-26). Animal studies of memory and learning with a known selective 5-HT6 antagonist found some positive effects (Rogers, D. C.; Hatcher, P. D.; Hagan, J. J. *Society of Neuroscience, Abstracts* 2000, 26, 680).

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901-5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Taken together, the above studies strongly suggest that compounds which are 5-HT6 receptor ligands may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a piperidinylchromen-6-ylsulfonamide derivative of formula I

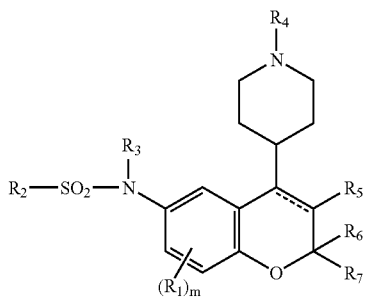

wherein
- $R_1$ is halogen, CN, $NO_2$, $OR_8$, $CO_2R_9$, $CONR_{10}R_{11}$ or a $C_1$-$C_6$alkyl, $C_2$-$C_6$alkenyl, $C_2$-$C_6$alkynyl, cycloalkyl, cycloheteroalkyl, aryl or heteroaryl group each optionally substituted;
- m is 0 or an integer of 1 or 2;
- $R_2$ is a $C_1$-$C_6$alkyl, cycloalkyl, cycloheteroalkyl, aryl or heteroaryl group each optionally substituted or an optionally substituted 8- to 13-membered bicyclic or tricyclic aromatic ring system having a N atom at the bridgehead and optionally containing 1, 2 or 3 additional heteroatoms selected from N, O, or S;
- $R_3$ and $R_4$ are each independently H or a $C_1$-$C_6$alkyl, $C_2$-$C_6$alkenyl, or $C_2$-$C_6$alkynyl group each optionally substituted;
- $R_5$, $R_6$ and $R_7$ are each independently H or a $C_1$-$C_6$alkyl, $C_2$-$C_6$alkenyl or $C_2$-$C_6$alkynyl group each optionally substituted;
- $R_8$ is H, $CO_2R_{12}$ or a $C_1$-$C_2$alkyl, $C_2$-$C_6$alkenyl, $C_2$-$C_6$alkynyl, aryl or heteroaryl group each optionally substituted;
- $R_9$ and $R_{12}$ are each independently H or a $C_1$-$C_6$alkyl, $C_2$-$C_6$alkenyl, $C_2$-$C_6$alkynyl, cycloalkyl, cycloheteroalkyl, aryl or heteroaryl group each optionally substituted;
- $R_{10}$ and $R_{11}$ are each independently H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted or $R_{10}$ and $R_{11}$ may be taken together with the atom to which they are attached to form an optionally substituted 5- to 8-membered ring optionally containing an additional heteroatom selected from O, N or S; and

----- represents a single bond or a double bond; or
a tautomer thereof, a stereoisomer thereof or a pharmaceutically acceptable salt thereof.

The present invention also provides a method and composition useful for the therapeutic treatment of a central nervous system disorder related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104-109, Pharma Press Ltd.

Surprisingly, it has now been found that piperidinylchromen-6-ylsulfonamide derivatives of formula I demonstrate 5-HT6 affinity. Advantageously, said sulfonamide derivatives may be used as effective therapeutic agents for the treatment of central nervous system (CNS) disorders associated with or affected by the 5-HT6 receptor. Accordingly, the present invention provides piperidinylchromen-6-ylsulfonamide derivatives of formula I

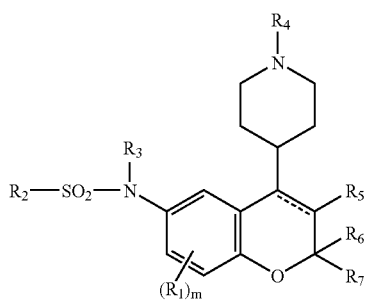

wherein
- $R_1$ is halogen, CN, $NO_2$, $OR_8$, $CO_2R_9$, $CONR_{10}R_{11}$ or a $C_1$-$C_6$alkyl, $C_2$-$C_6$alkenyl, $C_2$-$C_6$alkynyl, cycloalkyl, cycloheteroalkyl, aryl or heteroaryl group each optionally substituted;
- m is 0 or an integer of 1 or 2;
- $R_2$ is a $C_1$-$C_6$alkyl, cycloalkyl, cycloheteroalkyl, aryl or heteroaryl group each optionally substituted or an optionally substituted 8- to 13-membered bicyclic or tricyclic aromatic ring system having a N atom at the bridgehead and optionally containing 1, 2 or 3 additional heteroatoms selected from N, O, or S;
- $R_3$ and $R_4$ are each independently H or a $C_1$-$C_6$alkyl, $C_2$-$C_6$alkenyl, or $C_2$-$C_6$alkynyl group each optionally substituted;
- $R_5$, $R_6$ and $R_7$ are each independently H or a $C_1$-$C_6$alkyl, $C_2$-$C_6$alkenyl or $C_2$-$C_6$alkynyl group each optionally substituted;
- $R_8$ is H, $CO_2R_{12}$ or a $C_1$-$C_2$alkyl, $C_2$-$C_6$alkenyl, $C_2$-$C_6$alkynyl, aryl or heteroaryl group each optionally substituted;
- $R_9$ and $R_{12}$ are each independently H or a $C_1$-$C_6$alkyl, $C_2$-$C_6$alkenyl, $C_2$-$C_6$alkynyl, cycloalkyl, cycloheteroalkyl, aryl or heteroaryl group each optionally substituted;
- $R_{10}$ and $R_{11}$ are each independently H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted or $R_{10}$ and $R_{11}$ may be taken together with the atom to which they are attached to form an optionally substituted 5- to 8-membered ring optionally containing an additional heteroatom selected from O, N or S; and

----- represents a single bond or a double bond; or a tautomer thereof, a stereoisomer thereof or a pharmaceutically acceptable salt thereof.

As used in the specification and claims, the term halogen designates F, Cl, Br or I and the term cycloheteroalkyl designates a 5- to 7-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S; and R is H or an optional substituent as described hereinbelow:

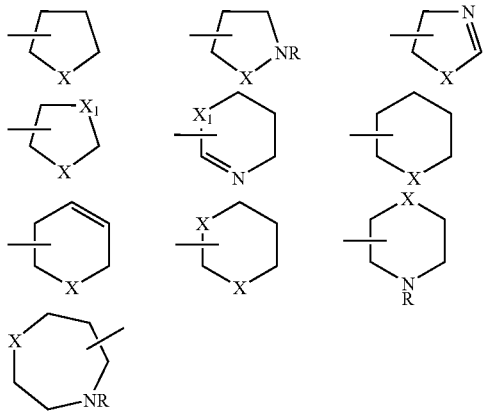

Similarly, as used in the specification and claims, the term heteroaryl designates a 5- to 10-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a carbocyclic aromatic ring system e.g., having 6 to 14 carbon atoms such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein W is NR, O or S; and R is H or an optional substituent as described hereinbelow:

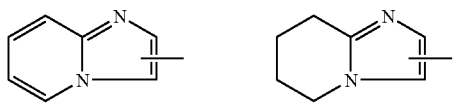

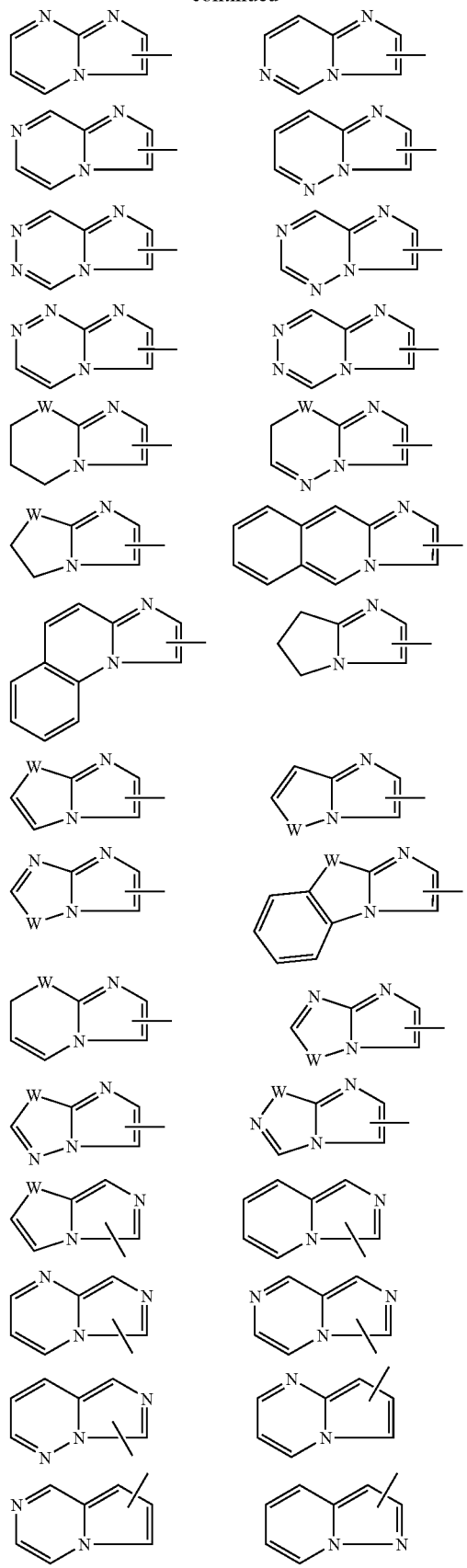

-continued

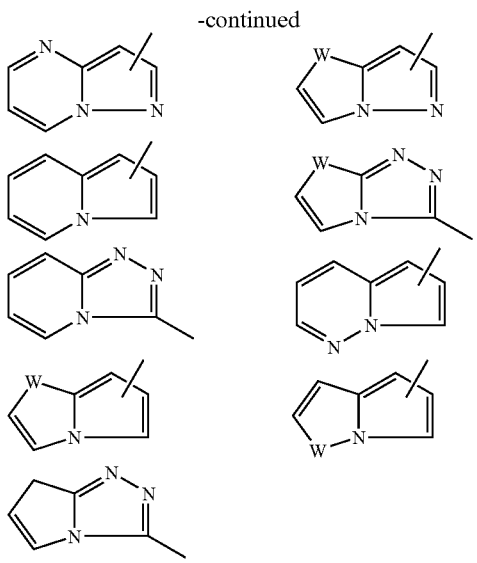

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl as designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl (such as heteroaryl or cycloheteroalkyl) or cycloalkyl groups, preferably halogen atoms or lower (e.g. $C_1$-$C_6$) alkyl groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers or in one or more tautomeric form. The various stereoisomers include enantiomers, diastereomers, atropisomers and geometric isomers. Tautomers include 4-alkylidene-2,3-dihydrochromenes or 4-alkyl-2H-chromenes.

One skilled in the art will appreciate that one stereoisomer or tautomer may be more active or may exhibit beneficial effects when enriched relative to the other stereoisomer(s) or tautomer(s) or when separated from the other stereoisomer(s) or tautomer(s). Additionally, the skilled artisan knows how to separate, enrich or selectively prepare said stereoisomers or tautomers. Accordingly, the present invention comprises compounds of Formula I, the stereoisomers thereof, the tautomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein

----- represents a double bond. Also preferred are those compounds of formula I wherein $R_2$ is an optionally substituted aryl or heteroaryl group. Another group of preferred compounds of formula I are those compounds wherein m is 0 or an integer of 1.

More preferred compounds of the invention are those formula I compounds wherein

----- represents a double bond and $R_2$ is an optionally substituted aryl or heteroaryl group. Another group of more preferred formula I compounds are those compounds wherein

----- represents a double bond; $R_2$ is an optionally substituted aryl or heteroaryl group; and $R_3$ and $R_4$ are each independently H or $CH_3$. A further group of more preferred formula I compounds are those compounds wherein m is 0 or an integer of 1 and $R_5$, $R_6$ and $R_7$ are H.

Preferred compounds of the invention include, but are not limited to:

N-(4-piperidin-4-yl-3,4-dihydro-2H-chromen-6-yl)benzenesulfonamide;
N-(4-piperidin-4-yl-2H-chromen-6-yl)benzenesulfonamide;
4-chloro-N-(4-piperidin-4-yl-2H-chromen-6-yl)benzenesulfonamide;
N-(4-piperidin-4-yl-2H-chromen-6-yl)naphthalene-1-sulfonamide;
5-chloro-N-[(4-piperidin-4-yl)-2H-chromen-6-yl]thien-2-ylsulfonamide;
3-bromo-N-[(4-piperidin-4-yl)-2H-chromen-6-yl]benzenesulfonamide;
N-[(4-methylpiperidin-4-yl)-2H-chromen-6-yl]benzenesulfonamide;
4-chloro-N-[(4-methylpiperidin-4-yl)-2H-chromen-6-yl]benzenesulfonamide;
N-[(4-methylpiperidin-4-yl)-2H-chromen-6-yl]naphthalene-1-sulfonamide;
a tautomer thereof;
a stereoisomer thereof; or
a pharmaceutically acceptable salt thereof.

Advantageously, the present invention provides a process for the preparation of a compound of formula I which comprises reacting a compound of formula II with a sulfonylchloride, $ClSO_2R_6$, in the presence of a base optionally in the presence of a solvent. The process of the invention is shown in flow diagram I.

Flow Diagram I

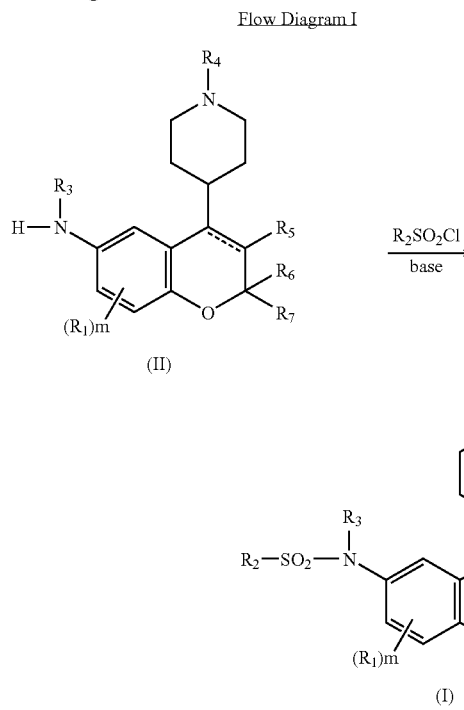

Bases suitable for use in the process of the invention include strong bases such as NaH, KOt-Bu, NaOH or any conventional base capable of removing a proton from a basic nitrogen atom.

Solvents suitable for use in the process of the invention include polar solvents such as dimethyl formamide, dimethyl sulfoxide, lower alkyl alcohol, acetonitrile, tetrahydrofuran, or the like.

Compounds of formula II may be prepared using conventional synthetic methods and, if required, standard separation or isolation techniques. For example, compounds of formula II wherein $R_4$ is other than H;

----- represents a double bond; and $R_3$ is H (IIa) may be prepared by reacting a 4-nitrophenol derivative of, formula III with a 3-chloropropionic acid of formula IV to give the O-alkylated compound of formula V; cyclizing the formula V compound with an appropriate dehydrating agent such as $P_2O_5/H_2SO_4$ to form a 6-nitro-4-chromanone of formula VI; reducing said 6-nitro formula VI compound via catalytic hydrogenation to give the corresponding 6-amino-4-chromanone of formula VII; and coupling said formula VII chromanone with a 4-piperidone compound of formula VIII to give the desired formula IIa intermediate. The reaction is shown in flow diagram II.

Flow Diagram II

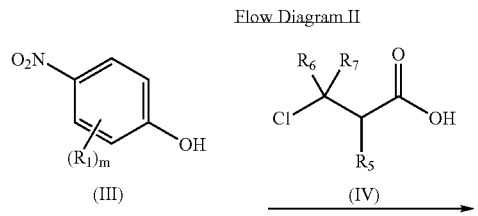

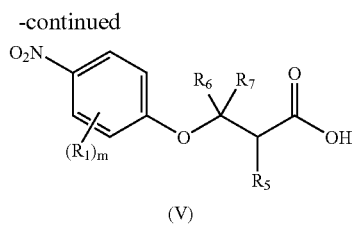

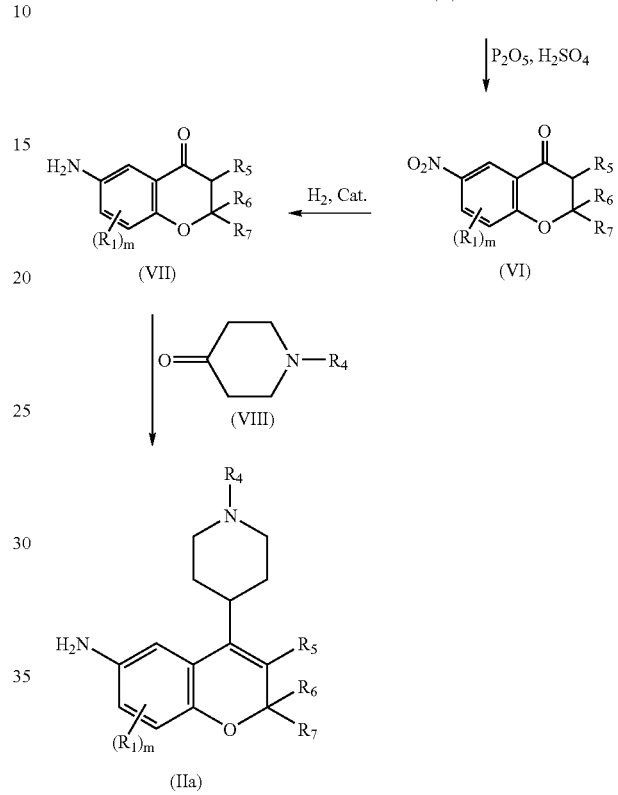

Compounds of formula II wherein

----- represents a single bond and $R_3$ represents H (IIb) may be prepared by reducing the formula IIa compound using conventional procedures such as treatment with formic acid in methanol in the presence of palladium to give the desired compound of formula IIb. The reaction is shown in flow diagram III.

Flow Diagram III

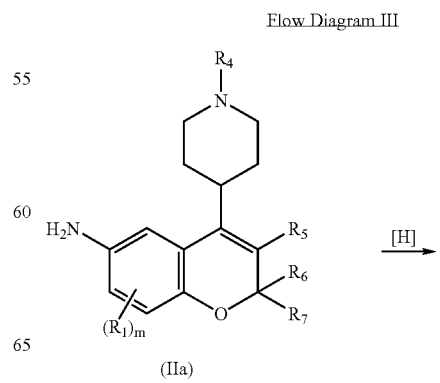

-continued

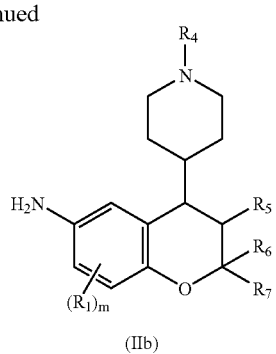

(IIb)

Compounds of formula I wherein $R_3$ and $R_4$ are H (Ia) may be prepared by coupling the amino chromanone compound of formula VII with a protected 4-piperidone compound of formula IX to give the compound of formula X; sulfonylating the protected formula X compound with an appropriate sulfonyl chloride, $R_2SO_2Cl$, to give the compound of formula XI; and deprotecting said formula XI compound to give the desired compound of formula Ia wherein

----- represents a double bond. Subsequent reduction using conventional techniques gives the compound of formula Ia wherein

----- represents a single bond. The reactions are illustrated in flow diagram IV wherein P represents a protecting group.

Flow Diagram IV

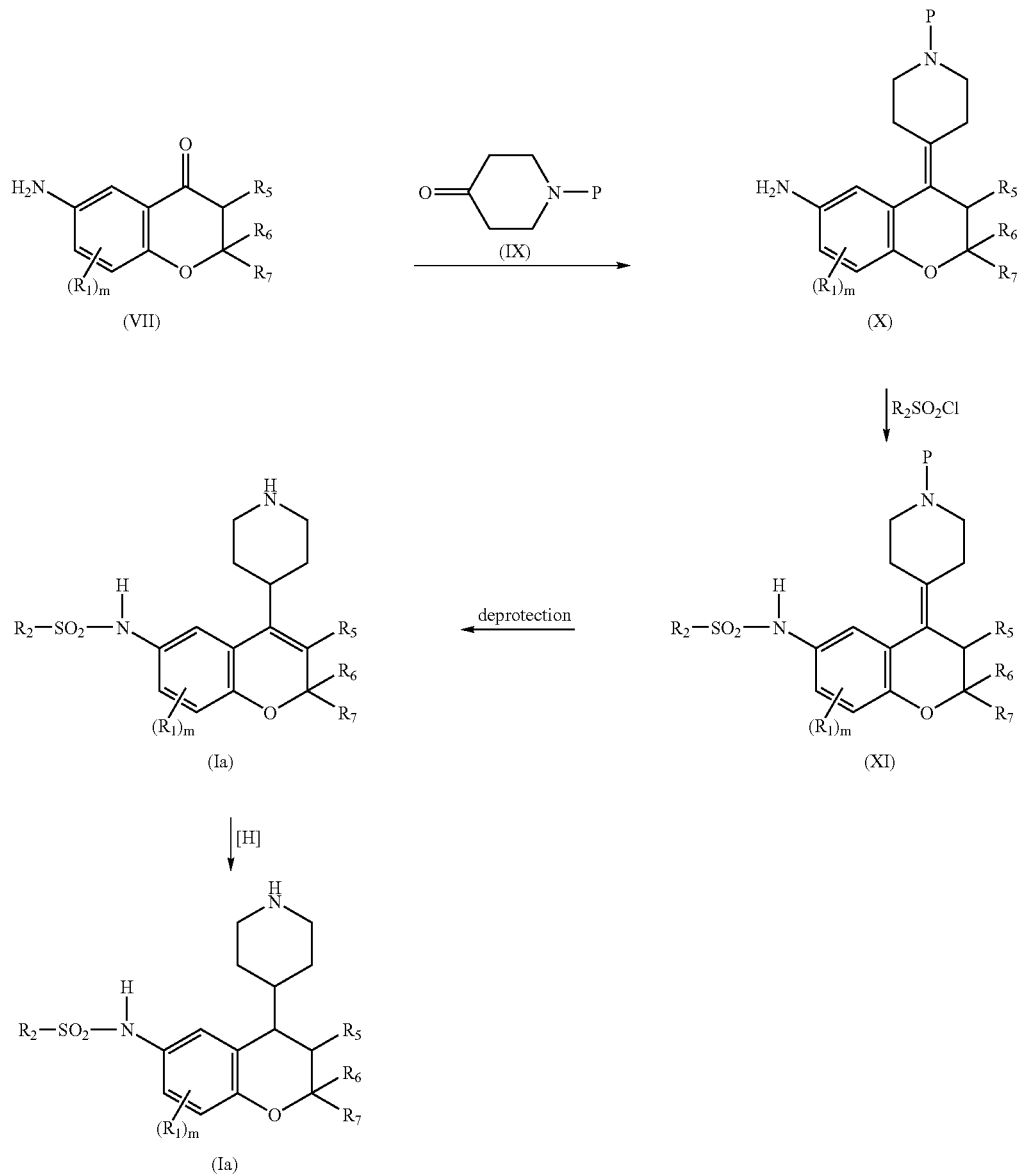

Alternatively, the compounds of formula VII may be sulfonylated to give a compound of formula XII and the formula XII compound may be coupled with the appropriate piperidone of formula VIII or formula XI to give a compound of formula I wherein

----- represents a double bond; and reducing said compound to give a compound of formula I wherein

----- represents a single bond. The reactions are shown in flow diagram V wherein $R_4$ is other than H.

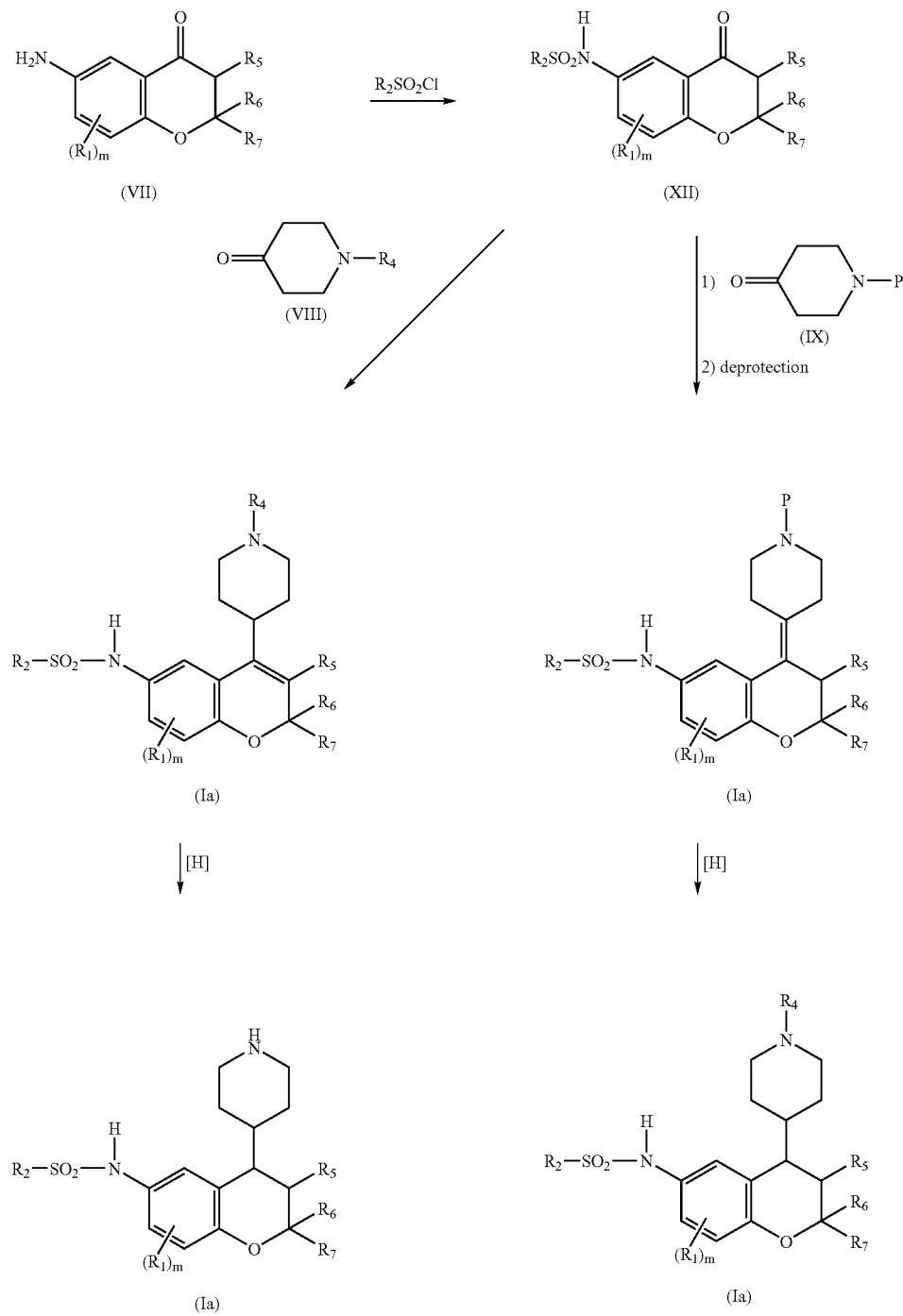

Flow Diagram V

Protecting groups suitable for use in the reactions shown hereinabove include benzyloxycarboxylate, t-butoxycarboxylate, benzyl, acetyl, or any conventional group known to protect a basic nitrogen in standard synthetic procedures.

Advantageously, the formula I compounds of the invention are useful for the treatment of CNS disorders relating to or affected by 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The term THF designates tetrahydrofuran. The term NMR designates proton nuclear magnetic resonance.

EXAMPLE 1

Preparation of 3-(4-Nitrophenoxy)propanoic Acid

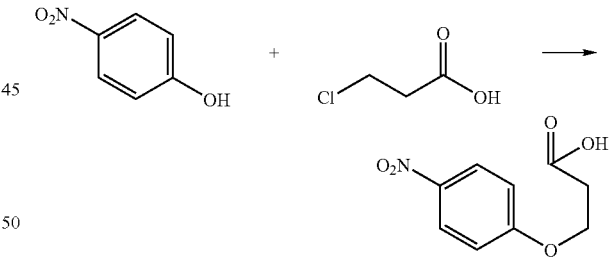

A mixture of 4-nitrophenol (14.0 g., 0.10 mol), 3-chloropropionic acid (10.8 g., 0.10 mol) and potassium hydroxide (11.2 g., 0.20 mol) in water and ethanol is heated at reflux temperature for 2 hours, cooled to ambient temperature, acidified with concentrated HCl to pH~1, and extracted with ethyl acetate. The organic phase is washed with a saturated aqueous solution of sodium bicarbonate. The aqueous bicarbonate phase is acidified with concentrated hydrochloric acid, and extracted with ethyl acetate. The final ethyl acetate extract is washed with brine, dried over MgSO$_4$ and concentrated in vacuo. The resultant residue is crystallized from ethyl ether and hexane to afford the title compound as an off-white crystalline solid, 5.3 g (25% yield), mp 117-118° C., identified by NMR and mass spectral analyses.

EXAMPLE 2

Preparation of
6-Nitro-2,3-dihydro-4H-chromen-4-one

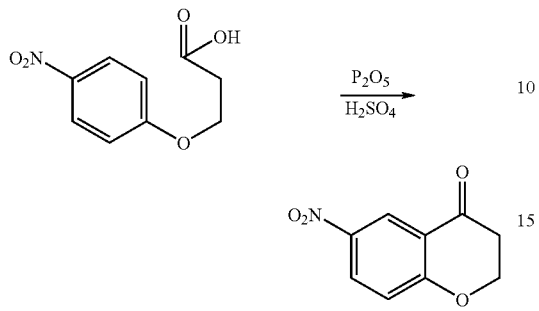

A mixture of 3-(4-nitrophenoxy)propanoic acid (6.5 g, 30 mmol), concentrated sulfuric acid (30 mL) and phosphorus pentoxide (5.2 g, 37 mmol) is stirred at 60° C. for 3 hours, poured onto ice, stirred for 15 minutes and extracted with ethyl acetate. The organic phase is washed with saturated aqueous sodium bicarbonate, dried over magnesium sulfate and concentrated in vacuo to afford the title compound as a beige solid, 5.5 g (94% yield) mp 171-173° C., identified by NMR and mass spectral analyses.

EXAMPLE 3

Preparation of
6-Amino-2,3-dihydro-4H-chromen-4-one

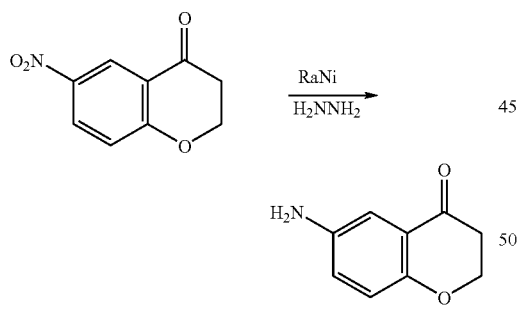

Under an inert atmosphere, a mixture of 6-nitro-2,3-dihydro-4H-chromen-4-one (5.4 g, 28 mmol), ethanol (250 mL), Raney nickel (1.5 g) and anhydrous hydrazine (8.8 mL, 0.28 mol) is stirred at ambient temperature overnight and filtered. The clear filtrate is concentrated to near dryness in vacuo. The resultant residue is treated with 6N hydrochloric acid and heated at reflux temperature for 1 hour, cooled in an ice bath, rendered basic with sodium bicarbonate and extracted with ethyl acetate. The organic phase is washed with brine, dried over $MgSO_4$ and concentrated in vacuo to afford the title compound as a yellow crystalline solid, 3.4 g (75% yield), mp 136-137° C., identified by NMR and mass spectral analyses.

EXAMPLE 4

Preparation of N-(4-Oxo-3,4-dihydro-2H-chromen-6-yl)benzenesulfonamide

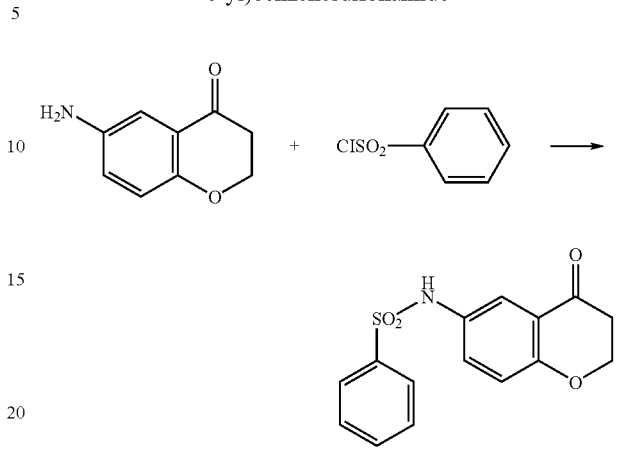

A solution of 6-amino-2,3-dihydro-4H-chromen-4-one (330 mg, 2.02 mmol) in $CH_2Cl_2$ is treated with pyridine (1 mL) and benzenesulfonyl chloride (0.28 mL, 2.2 mmol), stirred at ambient temperature for 1 hour, poured into dilute hydrochloric acid and extracted with ethyl acetate. The organic phase is washed sequentially with dilute hydrochloric acid until the pH of the wash is <2 and a saturated solution of sodium bicarbonate, dried over $MgSO_4$ and concentrated in vacuo to afford the title compound as a beige solid, 460 mg (74% yield), identified by NMR and mass spectral analyses.

EXAMPLES 5-12

Preparation of N-(4-Oxo-3,4-dihydro-2H-chromen-6-yl)arylsulfonamide Compounds

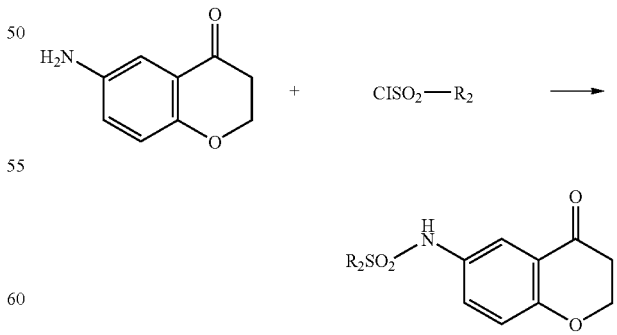

Using essentially the same procedure described in Example 4 hereinabove and employing the appropriate arylsulfonyl chloride, the compounds shown on Table I are obtained and identified by NMR and mass spectral analyses.

19

TABLE I

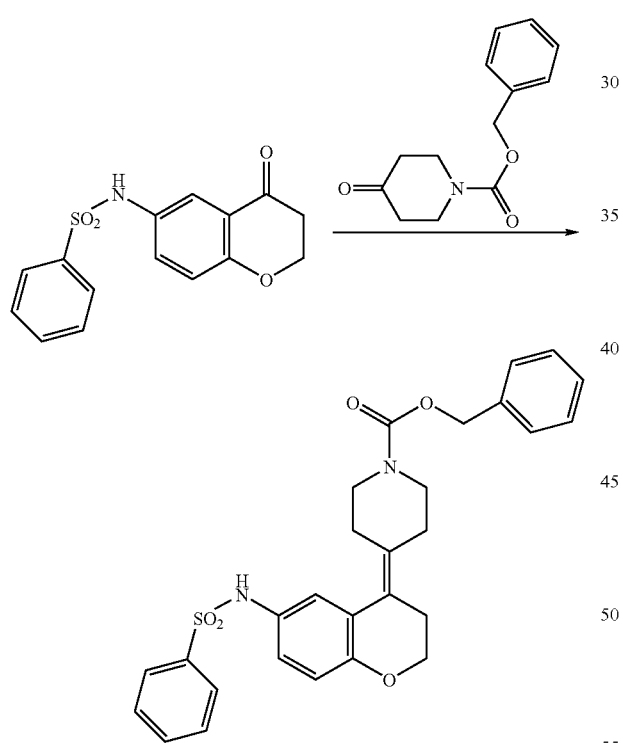

| Ex. No. | R2 | % Yield |
|---|---|---|
| 5 | 4-Cl—C6H4 | 100 |
| 6 | 1-naphthyl | 99 |
| 7 | 3-Cl—C6H4 | — |
| 8 | 2-naphthyl | — |
| 9 | 5-Cl-thien-2-yl | — |
| 10 | 6-Cl-imidazo[2,1-b][1,3]thiazol-5-yl | — |
| 11 | 4-F—C6H4 | — |
| 12 | 3-CF3—C6H4 | — |

EXAMPLE 13

Preparation of Benyzl 4-{6-[(Phenylsulfonyl)amino]-2,3-dihydro-4H-chromen-4-ylidine}piperidine-1-carboxylate Under an inert atmosphere, N-(4-oxo-3,4-dihydro-2H-chromen-6-yl)benzenesulfonamide (814 mg, 2.69 mmol) and 1-carbobenzyloxy-4-piperidone (690 mg, 2.96 mmol) are dissolved in THF, treated with zinc powder (785 mg, 12.1 mmol), cooled to 0° C., treated dropwise with titanium (IV) chloride (0.65 mL, 5.9 mmol) with cooling. When addition is complete, the mixture is heated to reflux temperature for 15 minutes, cooled to ambient temperature, treated with 2N hydrochloric acid (15 mL), and extracted with ethyl acetate. The organic phase is washed with a saturated aqueous solution of sodium carbonate, dried over magnesium sulfate and concentrated in vacuo. The resultant residue is chromatographed on basic alumina using 2% methanol in $CH_2Cl_2$ as eluent, to afford the title compound as a white solid foam, 540 mg (41% yield), identified by NMR and mass spectral analyses.

EXAMPLE 14

Preparation of N(4-Piperidin-4-yl-2H-chromen-6-yl)benzenesulfonamide Hemihydrate

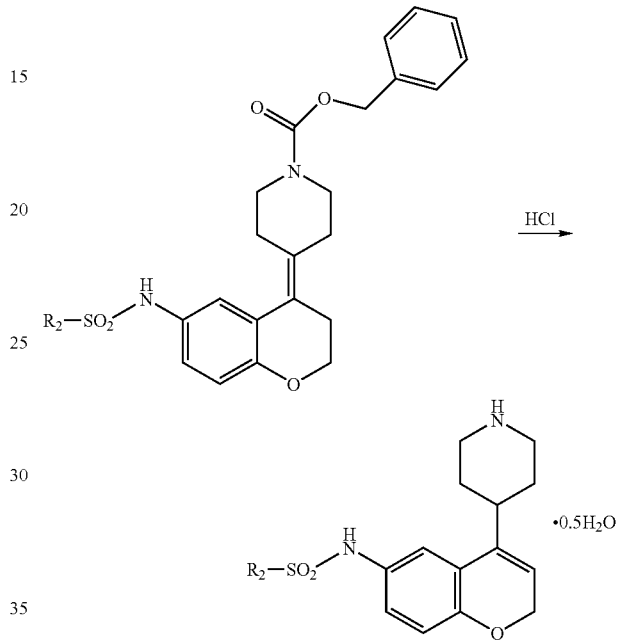

A mixture of benzyl 4-{6-[(phenylsulfonyl)amino]-2,3-dihydro-4H-chromen-4-ylidene}piperidine-1-carboxylate (500 mg, 1 mmol), ethanol (2 mL) and 6N hydrochloric acid (18 mL) is heated at reflux temperature for 2 hours, cooled to 0°-5° C., treated with 6N sodium hydroxide (14 mL) with cooling, then with saturated aqueous sodium carbonate to pH 9 and with chloroform. The organic phase is dried over $MgSO_4$ and concentrated in vacuo. The resultant residue is crystallized from ethanol to afford the title compound as an off-white solid, 75 mg (20% yield), mp >230° C., identified by NMR and mass spectral analyses.

EXAMPLES 15-22

Preparation of N(4-Piperidin-4-yl-2H-chromen-6-yl)arylsulfonamid Compounds

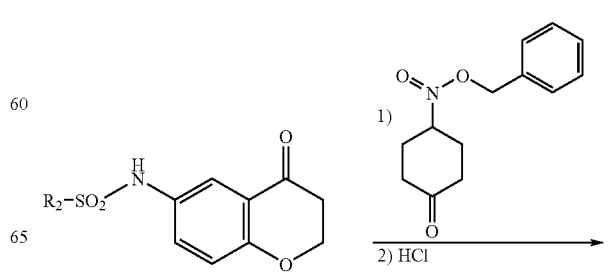

-continued

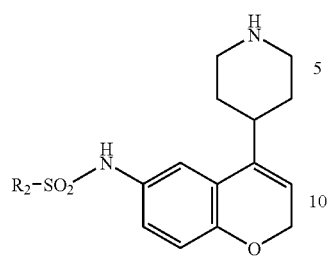

Using essentially the same procedures described in Examples 13 and 14 hereinabove and employing the appropriate N-(4-oxo-3,4,-dihydro-2H-chromen-6-yl)arylsulfonamide substrate, the compounds shown in Table II are obtained and identified by NMR and mass spectral analyses.

TABLE II

| Ex. No. | R2 | mp °C. | % Yield |
|---|---|---|---|
| 15 | 4-Cl—C$_6$H$_4$ | >240 | 43 |
| 16 | 1-naphthyl | >240 | 68 |
| 17 | 3-Cl—C$_6$H$_4$ | — | — |
| 18 | 2-naphthyl | — | — |
| 19 | 5-Cl-thien-2-yl | — | — |
| 20 | 6-Cl-imidazo[2,1-b][1,3]thiazol-5-yl | — | — |
| 21 | 4-F—C$_6$H$_4$ | — | — |
| 22 | 3-CF$_3$—C$_6$H$_4$ | — | — |

EXAMPLE 23

Preparation of N(4-Piperidin-4-dihydro-2H-chromen-6-yl)benzenesulfonamid Hydrochloride

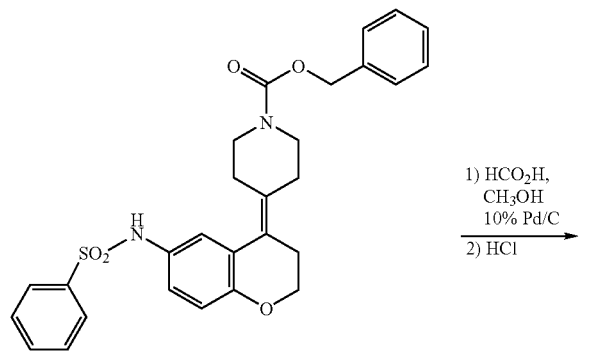

-continued

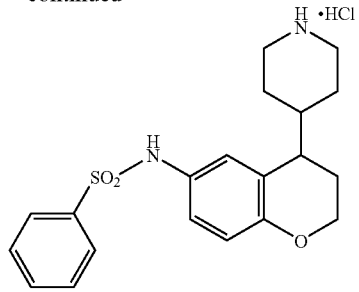

Under an inert atmosphere, a mixture of benzyl 4-{(phenylsulfonyl)amino]-2,3dihydro-4H-chromen-4-ylidene}piperidine-1-carboxylate (500 mg, 1 mmol) and 10% palladium on carbon (200 mg) in a 4.4% solution of formic acid in methanol (20 mL) is stirred at ambient temperature for 30 minutes and filtered through celite. The clear filtrate is evaporated to dryness in vacuo. The resultant residue is treated with a saturated aqueous solution of sodium bicarbonate and extracted with chloroform. The organic phase is dried over MgSO$_4$ and concentrated in vacuo to afford the free amine of the title compound as a clear oil, 230 mg (62% yield). Treatment of this oil with an ethereal solution of hydrogen chloride afforded the title compound as an off-white crystalline powder, mp>240° C., identified by NMR and mass spectral analyses.

EXAMPLES 24-31

Preparation of N(4-Piperidin-4-yl-3,4-dihydro-2H-chromen-6-yl)arylsulfonamid Compounds

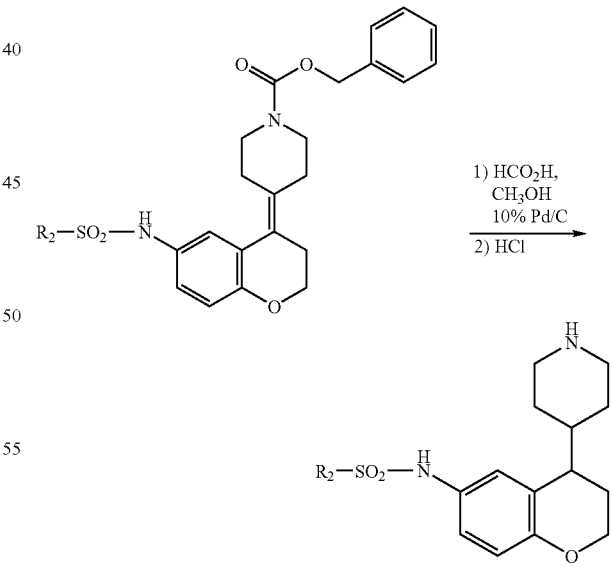

Using essentially the same procedure described in Example 23 hereinabove and employing the appropriate benzyl 4-{6-[(sulfonyl)amine]-2,3-dihydro-4H-chromen-4-ylidien}piperidine-1-carboxylate substrate, the compounds shown on Table III are obtained and identified by NMR and mass spectral analyses.

TABLE III

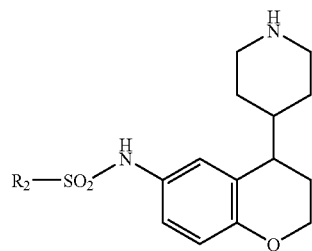

| Ex. No. | R2 |
|---|---|
| 24 | 4-Cl—$C_6H_4$ |
| 25 | 1-naphthyl |
| 26 | 3-Cl—$C_6H_4$ |
| 27 | 2-naphthyl |
| 28 | 5-Cl-thien-2-yl |
| 29 | 6-Cl-imidazo[2,1-b][1,3]thiazol-5-yl |
| 30 | 4-F—$C_6H_4$ |
| 31 | 3-$CF_3$—$C_6H_4$ |

EXAMPLE 32

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 µl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 µl. To each well is added the following mixture: 80.0 µl of incubation buffer made in 50 mM Tris.HCl buffer (pH 7.4) containing 10.0 mM $MgCl_2$ and 0.5 mM EDTA and 20 µl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 µl of tissue suspension. Nonspecific binding is measured in the presence of 10.0 µM methiothepin. The test compounds are added in 20.0 µl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table IV, below.

TABLE IV

| Test Compound (Ex. No.) | 5-HT6 Binding Ki (nM) |
|---|---|
| 14 | 1 |
| 15 | 2 |
| 16 | 2 |
| 23 | 12 |

| Comparative Examples | 5-HT6 Binding Ki (nM) |
|---|---|
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention demonstrate significant affinity for the 5-HT6 receptor.

What is claimed is:

1. A compound of formula I

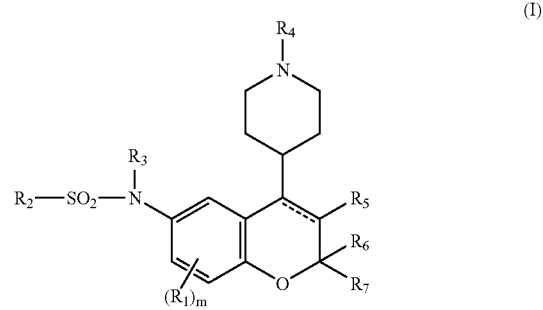

wherein
R$_1$ is halogen, CN, NO$_2$, OR$_8$, CO$_2$R$_9$, CONR$_{10}$R$_{11}$ or a C$_1$-C$_6$alkyl;
m is 0 or an integer of 1 or 2;
R$_2$ is an optionally substituted phenyl, naphthyl, thienyl or imidazo[2,1-b]thiazolyl group;
R$_3$ and R$_4$ are each independently H or C$_1$-C$_6$alkyl;
R$_5$, R$_6$ and R$_7$ are each independently H or C$_1$-C$_6$alkyl;
R$_8$ is H or a C$_1$-C$_2$alkyl;
R$_9$ is H or a C$_1$-C$_6$alkyl;
R$_{10}$ and R$_{11}$ are each independently H or a C$_1$-C$_6$alkyl; and

----- represents a single bond or a double bond; or
a stereoisomer thereof or a pharmaceutically acceptable salt thereof;
wherein the substituent groups which are optionally present are selected from the group consisting of hydrogen, halogen atoms, haloalkyl, hydroxyl, lower alkyl, alkoxy and alkylamino groups.

2. The compound according to claim 1 wherein

----- represents a double bond.

3. The compound according to claim 1 wherein m is 0 or an integer of 1.

4. The compound according to claim 1 wherein R$_5$, R$_6$ and R$_7$ are H.

5. The compound according to claim 2 wherein R$_3$ and R$_4$ are each independently H or CH$_3$.

6. The compound according to claim 5 wherein R$_2$ is an optionally substituted phenyl or naphthyl group.

7. The compound according to claim 6 wherein m is 0 and R$_5$, R$_6$ and R$_7$ are H.

8. The compound according to claim 1 selected from the group consisting of:
N-(4-piperidin-4-yl-3,4-dihydro-2H-chromen-6-yl)benzenesulfonamide;
N-(4-piperidin-4-yl-2H-chromen-6-yl)benzenesulfonamide;
4-chloro-N-(4-piperidin-4-yl-2H-chromen-6-yl)benzenesulfonamide;
N-(4-piperidin-4-yl-2H-chromen-6-yl)naphthalene-1-sulfonamide;
5-chloro-N-[(4-piperidin-4-yl)-2H-chromen-6-yl]thien-2-ylsulfonamide;
3-bromo-N-[(4-piperidin-4-yl)-2H-chromen-6-yl]benzenesulfonamide;
N-[(4-methylpiperidin-4-yl)-2H-chromen-6-yl]benzenesulfonamide;
4-chloro-N-[(4-methylpiperidin-4-yl)-2H-chromen-6-yl]benzenesulfonamide;
N-[(4-methylpiperidin-4-yl)-2H-chromen-6-yl]naphthalene-1-sulfonamide;
a stereoisomer thereof; and
a pharmaceutically acceptable salt thereof.

9. A pharmaceutical composition which comprises a pharmaceutically acceptable carrier and an effective amount of a compound of formula I

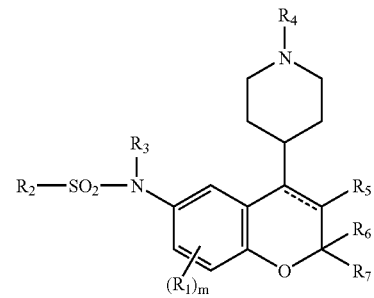

(I)

wherein
R$_1$ is halogen, CN, NO$_2$, OR$_8$, CO$_2$R$_9$, CONR$_{10}$R$_{11}$ or a C$_1$-C$_6$alkyl;
m is 0 or an integer of 1 or 2;
R$_2$ is an optionally substituted phenyl, naphthyl, thienyl or imidazo[2,1-b]thiazolyl group;
R$_5$, R$_6$ and R$_7$ are each independently H or C$_1$-C$_6$alkyl;
R$_8$ is H or a C$_1$-C$_2$alkyl;
R$_9$ is H or a C$_1$-C$_6$alkyl;
R$_{10}$ and R$_{11}$ are each independently H or a C$_1$-C$_6$alkyl; and

----- represents a single bond or a double bond; or
a stereoisomer thereof or a pharmaceutically acceptable salt thereof;
wherein the substituent groups which are optionally present are selected from the group consisting of hydrogen, halogen atoms, haloalkyl, hydroxyl, lower alkyl, alkoxy and alkylamino groups.

10. The composition according to claim 9 having a formula I compound wherein

----- represents a double bond.

11. The composition according to claim 9 having a formula I compound wherein m is 0.

12. The composition according to claim 11 having a formula I compound wherein R$_3$ and R$_4$ are each independently H or CH$_3$.

13. A process for the preparation of a compound of formula

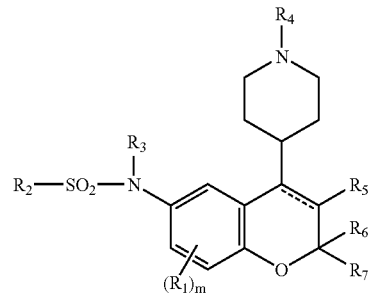

(I)

wherein
R$_1$ is halogen, CN, NO$_2$, OR$_8$, C$_2$R$_9$, CONR$_{10}$R$_{11}$ or a C$_1$-C$_6$alkyl;
m is 0 or an integer of 1 or 2;

$R_2$ is an optionally substituted phenyl, naphthyl, thienyl or imidazo[2,1-b]thiazolyl group;
$R_3$ is H;
$R_4$ is H or $C_1$-$C_6$alkyl;
$R_5$, $R_6$ and $R_7$ are each independently H or a $C_1$-$C_6$alkyl;
$R_8$ is H or a $C_1$-$C_2$alkyl;
$R_9$ is H or a $C_1$-$C_6$alkyl;
$R_{10}$ and $R_{11}$ are each independently H or a $C_1$-$C_6$alkyl; and

----- represents a single bond or a double bond wherein the substituent groups which are optionally present are selected from the group consisting of hydrogen, halogen atoms, haloalkyl, hydroxyl, lower alkyl, alkoxy and alkylamino groups;
which process comprises (i) or (ii) below:
(i) reacting a compound of formula VII with a protected 4-piperidone of formula IX, wherein $R_1$, $R_5$, $R_6$, $R_7$ and m are as described hereinabove and P is a protecting group:

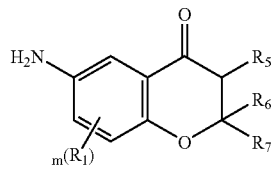

(VII)

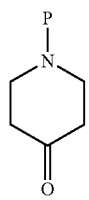

(IX)

to give a compound of formula X, wherein $R_1$, $R_5$, $R_6$, $R_7$, m and P are as described hereinabove:

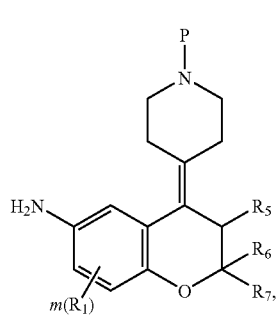

(X)

reacting said compound of formula X with an appropriate sulfonyl chloride, $R_2SO_2Cl$, wherein $R_2$ is as described hereinabove to give a compound of formula XI, wherein $R_1$, $R_2$, $R_5$, $R_6$, $R_7$, m and P are as described hereinabove:

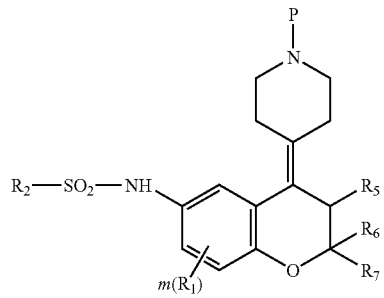

(XI)

and deprotecting said formula XI compound to give said compound of formula (I) above, wherein $R_3$ and $R_4$ of formula (I) are each H;
or
(ii) reacting said compound of formula VII with an appropriate sulfonyl chloride, $R_2SO_2Cl$, wherein $R_2$ is as described hereinabove, to give a compound of formula XII, wherein $R_1$, $R_2$, $R_5$, $R_6$, $R_7$ and m are as described hereinabove:

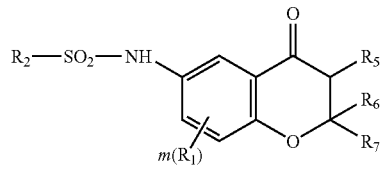

(XII)

and thereafter either coupling the formula XII compound with an appropriate piperidone of formula VIII:

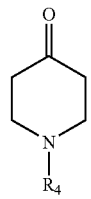

(VIII)

to give a compound of formula (I) wherein $R_3$ is H and $R_4$ is other than H as described hereinabove;
or coupling the formula XII compound with an appropriate piperidone of said formula IX, followed by deprotection to give a compound of formula (I) wherein $R_3$ is H and $R_4$ is other than H as described hereinabove.

* * * * *